(12) United States Patent
Lagos Wilson

(10) Patent No.: US 9,301,958 B2
(45) Date of Patent: Apr. 5, 2016

(54) USE AND APPLICATION OF A PHARMACEUTICAL COMPOSITION CONTAINING A MIXTURE OF NATURAL-ORIGIN HETEROCYCLICAL GUANIDINE

(75) Inventor: Nestor Antonio Lagos Wilson, Santiago (CL)

(73) Assignee: Phytotox Limited (BM)

( * ) Notice: Subject to any disclaimer, the term of this patent is extended or adjusted under 35 U.S.C. 154(b) by 0 days.

(21) Appl. No.: 13/487,722

(22) Filed: Jun. 4, 2012

(65) Prior Publication Data

US 2012/0238592 A1   Sep. 20, 2012

Related U.S. Application Data

(60) Continuation of application No. 11/338,156, filed on Jan. 24, 2006, which is a division of application No. 10/294,288, filed on Nov. 14, 2002, now abandoned.

(30) Foreign Application Priority Data

Nov. 15, 2001   (CL) .................................. 2764-2001

(51) Int. Cl.
| A61K 31/519 | (2006.01) |
| A61K 31/495 | (2006.01) |
| A61K 31/40 | (2006.01) |
| A61K 31/4168 | (2006.01) |
| A61K 31/52 | (2006.01) |
| A61K 38/48 | (2006.01) |

(52) U.S. Cl.
CPC .............. *A61K 31/519* (2013.01); *A61K 31/40* (2013.01); *A61K 31/4168* (2013.01); *A61K 31/495* (2013.01); *A61K 31/52* (2013.01); *A61K 38/4886* (2013.01)

(58) Field of Classification Search
CPC .. A61K 31/40; A61K 31/4168; A61K 31/495
USPC ........................................................ 514/267
See application file for complete search history.

(56) References Cited

U.S. PATENT DOCUMENTS

| 3,957,966 A | 5/1976 | Valan |
| 4,001,413 A | 1/1977 | Adams et al. |
| 4,029,794 A | 6/1977 | Adams et al. |
| 5,183,462 A | 2/1993 | Borodic |
| 5,298,019 A | 3/1994 | Borodic |
| 5,437,291 A | 8/1995 | Pasricha et al. |
| 5,504,117 A | 4/1996 | Gorfine |
| 5,562,907 A | 10/1996 | Amon |
| 5,674,205 A | 10/1997 | Pasricha et al. |
| 5,714,468 A | 2/1998 | Binder |
| 5,721,215 A | 2/1998 | Aoki et al. |
| 5,837,265 A | 11/1998 | Montal et al. |
| 5,908,746 A | 6/1999 | Suzuki et al. |
| 6,030,974 A | 2/2000 | Schwartz et al. |
| 6,117,877 A | 9/2000 | Fogel |
| 6,143,306 A | 11/2000 | Donovan |
| 6,187,756 B1 | 2/2001 | Lee et al. |
| 6,261,572 B1 | 7/2001 | Donovan |
| 6,299,893 B1 | 10/2001 | Schwartz et al. |
| 6,306,423 B1 | 10/2001 | Donovan et al. |
| 6,326,020 B1 | 12/2001 | Kohane et al. |
| 6,358,926 B2 | 3/2002 | Donovan |
| 6,407,088 B1 | 6/2002 | Dong et al. |
| 6,416,765 B1 | 7/2002 | Donovan |
| 6,432,986 B2 | 8/2002 | Levin |
| 6,447,787 B1 | 9/2002 | Gassner et al. |
| 6,552,191 B1 | 4/2003 | Zhou et al. |
| 6,559,154 B2 | 5/2003 | Kang et al. |
| 6,599,906 B1 | 7/2003 | Ku et al. |
| 6,780,866 B2 | 8/2004 | Ku et al. |
| 2001/0046962 A1 | 11/2001 | Graham |
| 2001/0053369 A1 | 12/2001 | Donovan |
| 2001/0053370 A1 | 12/2001 | Donovan |
| 2002/0025327 A1 | 2/2002 | Schmidt |
| 2002/0086036 A1 | 7/2002 | Walker |
| 2002/0142010 A1 | 10/2002 | Graham |
| 2002/0161013 A1 | 10/2002 | Liu et al. |
| 2002/0176872 A1 | 11/2002 | Aoki et al. |
| 2002/0192240 A1 | 12/2002 | Brooks et al. |
| 2002/0198226 A1 | 12/2002 | Ku et al. |
| 2003/0036502 A1 | 2/2003 | Gassner et al. |
| 2004/0009180 A1 | 1/2004 | Donovan |
| 2004/0018213 A1 | 1/2004 | Aoki et al. |
| 2004/0028706 A1 | 2/2004 | Aoki et al. |

FOREIGN PATENT DOCUMENTS

| CN | 1192903 | 9/1998 |
| CN | 1363275 | 8/2008 |
| WO | WO 9843619 | 10/1998 |
| WO | WO 9851290 | 11/1998 |

(Continued)

OTHER PUBLICATIONS

Abedrapo et al., Dis. Colon Rectum, vol. 47, No. 4, Apr. 2004, p. 598.
Munchau et al. "Uses of Botulinum Toxin Injection in Medicine Today", BMJ, vol. 320, pp. 161-165, Jan. 2000.
Borodic et al. "New Concepts in Botulinum Toxin Therapy", Drug Safety 11(3), pp. 145-152 (1994).
Andrinolo et al. "Toxicokinetics and Toxicodynamics of Gonyautoxins After an Oral Toxin Dose in Cats", Toxicon, vol. 40 (2001) pp. 699-709.
Bower et al., "Nonprotein Neurotoxins", Clinical Toxicology, vol. 18, No. 7, pp. 813-863 (1981).
Compagnon et al. "Accumulation of Paralytic Shellfish Poisoning Toxins . . . " Journal of Shellfish Research, 17 (1998) 67-73.
Lagos, N. Microalgal blooms: A global issue with negative impact in Chile. Biol. Res. 31 (1998) 375-386.

(Continued)

*Primary Examiner* — Yong Chong
(74) *Attorney, Agent, or Firm* — Wilmer Cutler Pickering Hale and Dorr LLP

(57) ABSTRACT

Pharmaceutical compositions comprising tricyclic 3,4-propinoperhydropurines and uses thereof for the treatment of facial wrinkling are provided.

12 Claims, 1 Drawing Sheet

(56) References Cited

FOREIGN PATENT DOCUMENTS

| WO | WO 0024419 | 5/2000 |
|----|------------|--------|
| WO | WO 0136588 | 5/2001 |

OTHER PUBLICATIONS

Andrinolo et al. "Paralyltic shellfish toxins in mussels and Alexandrium tamarense . . . ", Journal of Shellfish Research, 18 (1999): 203-209.

Andrinolo et al. "Toxic effects, pharmacokinetics, and clearance of saxitoxin . . . " Toxicon, 37:(1999) 447-464.

Andrinolo et al. "Paralytic shellfish poisoning (PSP) . . . " Seafood and Freshwater Toxins, 10 (2000) 203-215.

Compagnon et al., "Toxinas Paralizantes en microalgas . . . " Universidad de Concepcion, Chile, 2001:253-264.

Lagos, N. "Principales Toxinas de origen Fitoplanctonico . . . " Instituto Espanl de Oceanografia, 2002.

Andrinolo et al. "Toxicokinetics and toicodynamics of gonyautoxins alter an oral toxin does in cats." Toicon, 40 (2002) 1389-1387.

Androlino et al. "Transport of the organic cations gonyautoxin 2/3 epimers, a paralytic shellfish poison toxic . . . " Toxicon, 40 (2002) 1389-1397.

Botana, L. Seafood and Freshwater Toxins, Pharmacology, Physiology, and Detection. (2000) Marcel Dekker, Inc. 203-215.

Lagos et al. "Toxinas paralizantes in microalgas, un ejemplo de biodiversidad." Unversidad de Concepcion-Chile (2001) 253-264.

Lagos et al. "The first evidence of paralytic shellfish toxins in the freshwater cyanobacterium Cylindrospermopsis raciborskii . . . " Toxicon 37: 1359-1373.

Periera et al. "Paralytic Shellfish Toxins in the Freshwater Cyanobacterium Aphanizomenon flosaquae . . . " Toxicon 38: 1689-1702.

Rivas et al. "Biochemical characterization and inhibitory effects of dinophysistoxin-1 . . . " Bio. Res. 33 (2000) 197-206.

Uribe et al. "First report of Diarrhetic Shellfish Toxins in Magellanic Fjords, Southern Chile." Journal of Shellfish Research, vol. 20, No. 1, 69-74.

Borodic et al. "New Concepts in Botulinum Toxin Therapy." Drug Safety, 11:145-152 (1994).

Carruthers, A. "Update on Botulinum Toxin." Skin Therapy Letter, 4:1-2 (1999).

Carruthers et al. "Botulinum Toxin (Botox)Chemodenervation for Facial Rejuvenation." Facial Plastic Surgery Clinics of North America. 9:197-204.

Carruthers et al. "Botulinum A exotoxin use in clinical dermatology." Am. Acad. Dermatology. 34: 788-797.

Hall et al. "The Saxitoxins: Sourches Chemistry, and Pharmacology" in Marine Toxins: Origin, Structure and Molecular Pharmacology. Am. Chem. Society, pp. 29-65 (1990).

Jankovic et al. "Therapeutic Uses of Botulinum Toxin." New England Journal of Medicine. 324: 1186-1194.

Ken, C.Y. "Tetrodotoxin, Saxitoxin and Their Significance in the Study of Excitation Phenomena." Pharmacological Reviews 18: 997-1049.

Long et al. "Paralytic shellfish poisoning: A case report and serial electrophysicologic observations." Neurology 40:1310-1311.

Strichartz, "Structural Determinants of the Affinity of Saxitoxin for Neuronal Sodium Channels", J. Gen. Physiol 84:281-305.

Choudary et al. "Energetic Localization of Saxitoxin in its Channel Binding Site" Biophysical Journal Aug. 2002, Vo. 83, 912-19.

Heckmann, M., et al. "Botulinum toxin a in dermatology." Hautarzt, 1998 vol. 49, No. 2 pp. 87-90.

Giorgio et al., "A Comparison of Botulinum . . . for the Treatment of Chronic Anal Fissure", The New England Journal of Medicine, Jan. 1998, vol. 338, No. 4, pp. 217-220.

Ho et al., "The Role of Botulinum Toxin A in the Long-Term Prevention of Facial Wrinkles . . . " Otolarynology- Head and Neck Surgery, Aug. 1997, vol. 117, No. 2, p. 161.

Ikawa et al. "Toxin Profiles of the blue-green alga aphanizomen flos-aquae", Toxic Dinflagellates, Proc. Int. Conf. 3rd, pp. 299-304 (1985).

Wheeler, "Therapeutic Uses of Botulinum Toxin", American Family Physician, vol. 55, No. 2, pp. 541-545 (Feb. 1997).

Ates, O. Cayli, S.R., Article Neurological Res. Apr. 29, 2007(3): 317-23.

Barbier, Julian. Conotoxins targeting voltage-sensitive Na+ channels, Bacterial, Plant & Animal Toxins, 2003:127-145.

Gennenah, A.A., Shimizu, Y., Specific Toxicity of Paralyric Shellfish Poisons, Journal of Agriculture Chemistry, 1981, 29, 1289-1291.

Letienne, R., et al, Pharmacological characterisation of sodium channels in sinoatrial node pacemaking in the rat heart, Eur J. Pharmacol, Jan. 20, 2006:530(3):243-9.

Llewellyn, Lyndon E., Saxitoxin, a toxic marine natural product that targets a multitude of receptors, Nat. Prod. Rep., 2006, 23, pp. 200-222.

Nelson, M.D. Richard, A Systematic Review of Medical Therapy for Anal Fissure. Diseases of the Colon and Rectum. 2004, 47, pp. 422-431.

Oshima, Y., Post-Column derivatization HPLC methods for Paralytic Shellfish Poisons, Article.

Penzotti, Jennifer L. et al, Neosaxitoxin Interactions with the Na+Channel Outer Vestibule Determined by Mutant Cycle Analysis, Biophysical Journal, vol. 80 Feb. 2001, 698-706.

Rataud, Jean et al, Comparative study of voltage-sensitive sodium channel blockers in focal ischaemia and electric convulsions in rodents, Neuroscience Letters, vol. 172,Issues 1-2, May 19, 1994, pp. 19-23.

Schantz, E.J., et al. Properties and Use of Botulinum Toxin and Other Microbial Neurotoxins in Medicine, Microbiological Review. Mar. 1992, p. 80-99.

USE AND APPLICATION OF A PHARMACEUTICAL COMPOSITION CONTAINING A MIXTURE OF NATURAL-ORIGIN HETEROCYCLICAL GUANIDINE

CROSS REFERENCE TO RELATED APPLICATIONS

This application is a continuation of U.S. application Ser. No. 11/338,156, filed Jan. 24, 2006, which is a divisional of U.S. application Ser. No. 10/294,288 filed on Nov. 14, 2002. This application also claims priority under the Paris Convention for the Protection of Industrial Property to Chilean Patent Application Number 2764-2001, filed on Nov. 15, 2001 in the Department of Industrial Property in the Republic of Chile.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

This invention relates to pharmaceutical compositions containing heterocyclic guanidine-type compounds and uses thereof for blocking neuronal transmission. More specifically, this invention relates to tricyclic 3,4-propinoperhydropurines and uses thereof for blocking neuronal transmission.

BACKGROUND OF THE INVENTION

The presence of wrinkles in the neck and face of people are seen as negative aesthetic effects by social groups. These marks reflect face aging and increase the subjective awareness of the age of people. Since the beginning of civilization, natural or synthetic chemical compounds have been used and procedures have been developed (i.e. plastic surgery) to alleviate this problem. For example, plastic surgeons and cosmetic centers have been experimenting with and using Botulin A toxin as a pharmaceutical preparation that produces facial rejuvenation by removing face wrinkles Botulin A toxin is a neurotoxin that acts by chemiodenervation, or blocking the presynaptic release of the neurotransmitter acetylcholine in the neuromuscular plate, thus interfering with neuromuscular transmission, paralysing the muscle and preventing its contraction for a period of up to 4 months. Applied locally in the face of people, its effect is a facial rejuvenation that appears within 7-10 days after the toxin is applied, and has a duration of approximately 4 months. Botulin A toxin has been used for the treatment of diseases associated with muscular spasm, focal dystonia, sphincter relaxation (achalasia and anal fissure), hyperhydrosis and urinary bladder relaxation.

While Botulin A toxin is effective as a facial rejuvenate, it is an enzyme that is inherently unstable. This instability makes its use and handling complicated and less desirable. In fact, it requires freezing before using and must be used within four hours of opening the container. Because it is an enzyme, Botulin A toxin also generates antibodies that prevent its use in consecutive injections and can also induce an allergic response. In addition, its results are delayed 7-10 days, which is undesirable for patients wanting an immediate result. Accordingly, a need exists for a facial rejuvenate that is stable, fast-acting and that is not an enzyme.

SUMMARY OF THE INVENTION

In accordance with the objects of the invention, novel compositions and methods are provided. In one aspect of the invention, pharmaceutical compositions for interfering with neuronal transmission comprising an effective amount of at least one tricyclic 3,4-propinoperhydropurine are provided.

In a second aspect of the invention, preparations for facial rejuvenation are provided that comprise an effective amount of the composition of the invention and a facial cream.

In a third aspect of the invention, methods of interfering with neuronal transmission comprising contacting a neuron with an effective amount of the pharmaceutical compositions of the invention are provided.

In a fourth aspect of the invention, methods of interfering with muscle contracting comprising contacting a muscle with an effective amount of the composition of the invention are provided.

DETAILED DESCRIPTION OF THE DRAWINGS

FIG. 1 is an illustration of an application pattern for the treatment of a human face.

DETAILED DESCRIPTION OF THE INVENTION

In accordance with the present invention, it has been discovered that compositions comprising heterocyclic guanidine-type compounds, and more specifically tricyclic 3,4-propinoperhydropurines, can be used for many cosmetic or clinical applications, without any surgery, side effects, allergies, immune rejection or hematoma. The compositions of the invention may be used to treat conditions including, but not limited to blepharospasm, strabismus, focal dystonia, sphinceter relaxation (achalasia and anal fissure), hyperhydrosis, urinary bladder relaxation, muscular spasm-related pain management, muscular spasms, improved wound healing and facial wrinkling. In accordance with the present invention, muscular relaxation is immediate, usually occurring in less than five minutes.

The compositions of the invention comprise an effective amount of at least one tricyclic 3,4-propinoperhydropurine represented by the following structure:

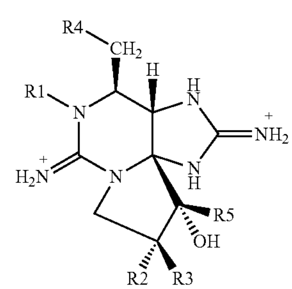

wherein $R_1$ and $R_5$ are independently H or OH; $R_2$ and $R_3$ are independently H or $OSO_3$; and R4 is independently $COONH_2$, OH, H, $COONHSO_3$ or $COOCH_3$; and a pharmacologically acceptable carrier. These tricyclic 3,4-propinoperhydropurines may be purified from dinoflagellates, cyanobacterias and also may be accumulated by highly contaminated mollusks, which are also temporary muscular relaxants when locally injected. Any pharmacologically acceptable carrier may be used, including but not limited to water. The compounds of the invention are generally diluted in a solution of acetic acid or 0.09% sodium chloride.

As used herein, "an effective amount" is that amount sufficient to interfere with neuronal transmission by blocking the presynaptic release of the neurotransmitter acetylcholine in the neuromuscular plate, thus interfering with transmission, paralysing the muscle and preventing it from contracting, or producing a relaxation of contracted muscles. For example, an effective amount of the compositions of the invention may be a 100 to 800 microliter dose of forty units per milliliter solution of tricyclic 3,4-propinoperhydropurines. The unit of activity is the amount of the composition of the invention necessary to block the muscular contractions of the crural biceps of a mouse leg for 1.5 to 2.0 hours. The compounds of the invention are generally diluted with a 10 mM (millimolar), pH 4 solution of acetic acid. In one specific embodiment of the invention, the compositions of the invention comprise 40 units per milliliter of a 10 mM, pH 4 solution of acetic acid.

In one embodiment of the invention, and with reference to Table 1 below, the pharmaceutical compositions of the invention comprise Saxitoxin. In a second embodiment of the invention, the pharmaceutical compositions of the invention comprise Gonyautoxin 2. In a third embodiment of the invention, the pharmaceutical compositions of the invention comprise Gonyautoxin 3. In a forth embodiment of the invention, the pharmaceutical compositions of the invention comprise Gonyautoxin 4. In a fifth embodiment of the invention, the pharmaceutical compositions of the invention comprise Gonyautoxin 5. In a sixth embodiment of the invention, the pharmaceutical compositions of the invention comprise neoSaxitoxin. In a seventh embodiment of the invention, the pharmaceutical compositions of the invention comprise Gonyautoxin 1. In an eighth embodiment of the invention, the pharmaceutical compositions of the invention comprise Decarbamoyl-Saxitoxin.

TABLE 1

Tricyclic 3,4-propinoperhydropurines

| Compound | $R_1$ | $R_2$ | $R_3$ | $R_4$ | $R_5$ |
|---|---|---|---|---|---|
| Saxitoxin | H | H | H | $COONH_2$ | OH |
| neoSaxitoxin | OH | H | H | $COONH_2$ | OH |
| Decarbamoyl-Saxitoxin | OH | H | H | OH | OH |
| Gonyautoxin 1 | OH | H | $OSO_3^-$ | $COONH_2$ | OH |
| Gonyautoxin 2 | H | H | $OSO_3^-$ | $COONH_2$ | OH |
| Gonyautoxin 3 | H | $OSO_3^-$ | H | $COONH_2$ | OH |
| Gonyautoxin 4 | OH | $OSO_3^-$ | H | $COONH_2$ | OH |
| Gonyautoxin 5 | H | H | H | $COONHSO_3^-$ | OH |

In specific embodiments of the invention, the pharmaceutical compositions comprise a mixture of tricyclic 3,4-propinoperhydropurines. The compounds are purified and used individually and/or mixed together. In one preferred embodiment, the pharmaceutical compositions of the invention comprise a mixture of Gonyautoxin 2, Gonyautoxin 3, and Saxitoxin. In another preferred embodiment, the pharmaceutical compositions of the invention comprise a mixture of Gonyautoxin 4, Gonyautoxin 1, Gonyautoxin 5, Gonyautoxin 3 and Gonyautoxin 2. In yet another preferred embodiment, the pharmaceutical compositions of the invention comprise neoSaxitoxin and Gonyautoxin 2. In still another preferred embodiment, the pharmaceutical compositions of the invention comprise a mixture of Saxitoxin, neoSaxitoxin; Decarbamoyl-Saxitoxin, Gonyautoxin 3 and Gonyautoxin 2. It should be understood by those of skill in the art that other mixtures and combinations of tricyclic 3,4-propinoperhydropurines are within the scope of this invention.

In one embodiment of the invention, the compounds of the invention are used in combination with an effective amount of Botulin A toxin. In this embodiment, the pharmaceutical compositions of the invention comprise an effective amount of Botulin A toxin and an effective amount of at least one tricyclic 3,4-propinoperhydropurine. The combination may be used in any cosmetic or clinical application in which the compounds of the invention, or Botulin A toxin are used, for example, blepharospasm, strabismus, focal dystonia, sphincter relaxation (achalasia and anal fissure), hyperhydrosis, urinary bladder relaxation, muscular spasm-related pain management, muscular spasms, improved wound healing, and facial wrinkle removal.

These pharmaceutical compositions of the invention may be used for many cosmetic and clinical applications including, but not limited to blepharospasm, strabismus, focal dystonia, sphincter relaxation (achalasia and anal fissure), hyperhydrosis, urinary bladder relaxation, muscular spasm-related pain management, muscular spasms, improved wound healing, and facial wrinkle removal. Generally, the pharmaceutical compositions of the invention are applied locally in the form of preparations. To form preparations, an effective amount of the pharmaceutical compositions of the invention are added to a facial cream complete with its coadjuvants. Unlike Botulin A toxin, these preparations are stable at room temperature, do not require refrigeration, are sterilizable, do not generate antibodies, are not peptide in nature, act immediately, and may be injected repeatedly without any side effects.

Without being bound by theory, when applied locally, these compounds carry out their antispasmodic action by blocking the spreading of nervous impulse, or neuronal transmission, by reversibly binding to the sole biological molecular receptor, i.e. the voltage gated sodium channel, present in all neurons and excitable cells. By binding to this channel, there is no entry of sodium to the neuronal cell; depolarization does not occur and, therefore, propagation of the impulse is stopped. This action mechanism blocks the presynaptic release of the neurotransmitter acetylcholine in the neuromuscular plate, thus interfering with neuromuscular transmission, paralysing the muscle and preventing it from contracting, or producing a relaxation of muscles contracted by pathological problems. This mechanism is particularly efficient for cosmetic purposes, as it does not let some facial muscles contract, all of them associated with and responsible for the formation of wrinkles, thus producing the sought-after effect of facial rejuvenation.

The pharmaceutical preparations of the invention are applied locally around the muscle that is to be paralysed or prevented from contracting. The application should be in amounts of no more than one milliliter in different places around the muscle, particularly around the areas of greatest innervations. The unit of activity is the amount of the compositions of the invention necessary to block the contractions of the crural biceps of a mouse leg for 1.5 to 2 hours. The preferred dosage rate is 100 to 800 microliters per injected point, depending on the size, irrigation and anatomical location of the muscle, while maintaining a concentration of 20-40 units/milliliter. The effect is immediately apparent, generally occurring a maximum of thirty seconds after injection. The maximum effect may be seen within 15 minutes. Its effective duration depends on the dose administered, the muscle in question, as well as the volume and specific composition administered. This is the pattern for all clinical applications and pathologies. The injection may be accomplished by using a 1 milliliter, tuberculin-type disposable syringe with a twenty-seven to thirty gauge needle. In the case of strabismus, a dose of twenty to forty units in a volume of 50-100 microliters may be injected in the orbicular muscle. Use of the pharmaceutical preparations of the invention is limited to individuals over twelve years old. There is no contraindication for pregnant women.

The advantageous properties of this invention can be observed by reference to the following example, which is meant to illustrate, and not limit, the invention in any way.

Example

Before the application, a photographic record is made of the person to be treated, first with her face resting and relaxed, and then, frowning and producing a maximum facial contraction. The person then places ice on their forehead and on the two lateral zones where the preparation is to be injected. With reference to FIG. 1, the application should follow a specific pattern. A volume is injected alongside each black-dot injection point shown in FIG. 1. A pharmaceutical composition comprising a (2:1:1 volume/volume) mixture of Gonyautoxin 2, Gonyautoxin 3 and Saxitoxin mixture is applied at a dose of 40 units/milliliter. Each injection is made with a 1 milliliter, tuberculin-type disposable syringe with a 27-30 gauge needle. After injecting, the point of injection is disinfected with a gauze soaked in bi-alcohol or in any other disinfectant. The total amount required to complete the face treatment is 1.7 milliliters.

The expected result is an immediate inability to frown and to show lines when the face is resting. The person experiences a feeling of facial stretching similar to that felt when applying a facial cream mask. After that, ice is applied on the injected zones for five minutes. Thirty minutes after the application, the patient gets used to the feeling of facial stretching. At that time, the person walks out with no discernible wrinkles, a rejuvenated facial look, no face marks or hematoma, and completely normal. The face recovers its normal color within twenty minutes, depending on how relaxed the injected patient has become. The whole application procedure takes ten minutes at the most, and produces a very slight pain from the needle and the injected solution. The pain disappears as soon as the syringe is withdrawn. There are no traumas of any kind, nor any sequelae. The patient may be checked the next day and every fifteen days thereafter. At this dose, the effect lasts for one month. After the first month, the treatment may be repeated as often as necessary.

In view of the above, it will be seen that all the objects and features of the present invention are achieved, and other advantageous results obtained. The examples and description of the invention contained herein is illustrative only, and is not intended in a limiting sense.

What is claimed is:

1. A method of treating facial wrinkling comprising administering a therapeutically effective amount of a composition consisting of Gonyautoxin 2 and Gonyautoxin 3 and a pharmaceutically acceptable carrier, wherein said administering is without trauma or sequelae.

2. The method of claim 1, wherein the carrier is acetic acid.

3. The method of claim 1, wherein the composition is administered via injection at the site of the facial wrinkling.

4. The method of claim 3, wherein the amount of the composition injected is one milliliter with a concentration of 20-40 units per milliliter.

5. The method of claim 1, wherein the composition is applied locally in the form of a preparation.

6. The method of claim 5, wherein the preparation is a facial cream.

7. A method of treating facial wrinkling comprising administering a therapeutically effective amount of a composition consisting of an active ingredient selected from the group consisting of Gonyautoxin 1, Gonyautoxin 2, Gonyautoxin 3, Gonyautoxin 4, Gonyautoxin 5, and combinations thereof, and a pharmaceutically acceptable carrier, wherein said administering is without trauma or sequelae.

8. The method of claim 7, wherein the carrier is acetic acid.

9. The method of claim 7, wherein the composition is administered via injection at the site of the facial wrinkling.

10. The method of claim 9, wherein the amount of the composition injected is one milliliter with a concentration of 20-40 units per milliliter.

11. The method of claim 7, wherein the composition is applied locally in the form of a preparation.

12. The method of claim 11, wherein the preparation is a facial cream.

\* \* \* \* \*